United States Patent [19]
Kretzschmar et al.

[11] Patent Number: 5,607,403
[45] Date of Patent: Mar. 4, 1997

[54] DISPOSABLE NEEDLECAP HOLDER

[75] Inventors: James L. Kretzschmar; Deborah A. Kretzschmar, both of Alamogordo, N.M.

[73] Assignee: The United States of America as represented by the Secretary of the Air Force, Washington, D.C.

[21] Appl. No.: 640,581

[22] Filed: Apr. 5, 1996

Related U.S. Application Data

[63] Continuation-in-part of Ser. No. 427,463, Apr. 21, 1995, abandoned.

[51] Int. Cl.$^6$ ................................................ A61M 5/32
[52] U.S. Cl. .................... 604/263; 604/192; 128/919; 206/365
[58] Field of Search .................... 604/187, 192, 604/263, 110; 206/365, 366; 128/919

[56] References Cited

U.S. PATENT DOCUMENTS

| | | | |
|---|---|---|---|
| 4,380,292 | 4/1983 | Cramer | 604/192 |
| 4,681,567 | 7/1987 | Masters et al. | 604/198 |
| 4,802,645 | 2/1989 | Chiodo | 248/309.1 |
| 4,810,248 | 3/1989 | Masters et al. | 604/192 |
| 4,919,656 | 4/1990 | Bracker et al. | |
| 4,936,449 | 6/1990 | Conard et al. | 206/366 |
| 4,950,249 | 8/1990 | Jagger et al. | 604/192 |
| 4,955,865 | 9/1990 | Steiner et al. | 604/192 |
| 4,955,866 | 9/1990 | Corey | 604/192 |
| 4,986,816 | 1/1991 | Steiner et al. | 604/192 |
| 4,994,046 | 2/1991 | Wesson et al. | 604/198 |
| 5,067,945 | 11/1991 | Ryan et al. | 604/198 |
| 5,078,692 | 1/1992 | Cuprak | 604/192 |
| 5,078,695 | 1/1992 | Farrar, Jr. et al. | 604/192 |
| 5,143,414 | 9/1992 | Rosellini | 294/99.2 |
| 5,167,643 | 12/1992 | Lynn | 604/263 |
| 5,207,653 | 5/1993 | Janjua et al. | 604/192 |
| 5,209,738 | 5/1993 | Bruno | 604/263 X |
| 5,295,975 | 3/1994 | Lockwood, Jr. | 604/198 |
| 5,304,148 | 4/1994 | Lannoye et al. | 604/192 |
| 5,311,985 | 5/1994 | Suida | 206/210 |
| 5,336,199 | 8/1994 | Castillo et al. | 604/198 |
| 5,399,169 | 3/1995 | Stein | 604/192 |

*Primary Examiner*—John D. Yasko
*Attorney, Agent, or Firm*—Fredric L. Sinder; Thomas L. Kundert

[57] ABSTRACT

A new disposable needlecap holder for safe, one-handed recapping of hypodermic syringe needles is disclosed. The needlecap holder is a generally rectangular solid having a back face with an adhesive surface so that the solid can be attached to a horizontal or vertical surface, such as a table, cart or wall. A front face on the solid has an opening for a bore that extends through the solid toward the back face. The bore is sized to hold a needlecap. A bullseye ring surrounds the bore opening. The back face is at an acute angle to the front face. To use, the back face is attached to a flat surface and a needlecap inserted into the bore. Using the bullseye ring as a guide, a healthcare worker inserts a needle into the held needlecap until it snaps into place. The needlecap holder can be made of any lightweight disposable plastic material.

4 Claims, 1 Drawing Sheet

DISPOSABLE NEEDLECAP HOLDER

RIGHTS OF THE GOVERNMENT

The invention described herein may be manufactured and used by or for the Government of the United States for all governmental purposes without the payment of any royalty.

This application is a continuation-in-part of application Ser. No. 08/427,463, filed on Apr. 21, 1995 now abandoned.

BACKGROUND OF THE INVENTION

The present invention relates generally to hypodermic syringes, and more specifically to a needlecap holder for safely replacing a needlecap over the needle of a hypodermic syringe.

The risks from being accidentally pricked by a used hypodermic syringe needle, generally called a needlestick accident, are well-known. In addition to the obvious risk from a needlestick, there has been a concern over any contact with a used, or contaminated, needle. These risks are especially present when replacing a needlecap onto a hypodermic syringe. The usual method for replacing a needlecap is to hold the syringe in one hand and the cap in the other while moving one or both hands together until the cap snaps into place over the needle. An obvious disadvantage of this method is that it requires two hands. Another disadvantage is that there is a very high potential for missing and pricking the fingers holding the cap.

Another usual method for replacing a needlecap is to lay the needlecap horizontally on an instrument tray or other flat surface, then move the syringe with one hand toward the resting needlecap until the needle is covered, and finally using the other hand to push the needlecap until it snaps into place. The first problem with this method is that the needlecap moves about, making it difficult to cover the needle. The second problem is that once the needle is covered, two hands are again needed to securely snap the needlecap in place. A particular disadvantage of this method is that it is both very awkward and dangerous to attempt to maneuver an uncapped syringe in a horizontal position to hit an unstable target.

The prior art is replete with attempts to reduce the risk of needlestick accidents. A good example is U.S. Pat. No. 5,304,148 to Lannoye et al. The Lannoye et al. patent discloses a needlecap with an expandable umbrella-like shield surrounding the open end of the needlecap. When using the usual two-handed movement to replace a needlecap, the shield reduces the risk that missing the open end of the needlecap with the needle will result in a needlestick accident. A similar example is U.S. Pat. No. 5,078,692 to Cuprak. Cuprak discloses a shielded holder for holding a conventional needlecap. The Cuprak holder can be collapsed for storage. Another good example is U.S. Pat. No. 5,207,653 to Janjua et al. The Janjua et al. patent discloses a combination needle and needlecap in which the needlecap is hinged at the needle hub and has a longitudinal slit so that the cap can be easily pivoted to cover or uncover the needle. A similar device, disclosed in U.S. Pat. No. 4,950,249 to Jagger et al., uses a two-piece needlecap hinged clamshell-like at the needle hub to cover and uncover the needle. U.S. Pat. No. 5,143,414 to Rosellini discloses a pair of pliers specially adapted to pick up and hold a needlecap at a safe distance from one hand while the other hand assists in reinserting the needle. U.S. Pat. No. 4,994,046 to Wesson et al. discloses a clip that snaps around the body of a syringe and includes a flexible plastic extension having an end which fits over the tip of the needle. When the needle is extended, the extension end flexes away from the needle tip. When the needle is drawn back, the extension end flexes back over the needle tip to reduce the danger of a needlestick accident. An example of another approach is shown in U.S. Pat. No. 5,295,975 to Lockwood, Jr. The Lockwood, Jr. patent discloses an extension for a hypodermic syringe that includes a sliding outer cover that extends to cover the needle after use. Another approach is shown in U.S. Pat. No. 5,336,199 to Castillo et al. The Castillo et al. patent discloses a spring-urged telescoping needlecap that automatically retracts and extends as the needle is inserted into a patient. The telescoping needlecap includes an internal absorbent wiper for removing any bodily fluid that remains on the outside of the needle to prevent an aerosol spray from the needle following withdrawal from a patient's body as the sheath assembly actuates and extends to cover the needle.

Analyzing the prior art reveals that it attempts to solve the problem of the risk of needlestick accidents generally in one of two ways. First, by protecting the hand holding the needlecap by providing a handheld apparatus for more safely holding the needlecap during recapping. Or, second, by attempting to eliminate the need for the second hand holding the needlecap by making the needlecap, or the combination needlecap-syringe, structurally more complex.

Unfortunately, these and other prior art attempts to reduce the risk of needlestick accidents have not found wide acceptance. They add an unwelcome complexity to what most busy healthcare workers expect should be a straight-forward procedure, require replacing conventional hypodermic syringe parts with complex and costly new components, or both.

Thus it is seen that there is still a need for apparatus and methods for reducing the risks of replacing a needlecap on a hypodermic syringe, but which do not add unwanted complexity or require modification of existing needlecaps and syringes.

It is, therefore, a principal object of the present invention to provide an apparatus for making safer replacing a needlecap on a hypodermic syringe and that performs its function unobtrusively and without requiring modification of existing needlecaps and syringes.

It is a feature of the present invention that it only needs one hand to operate.

It is another feature of the present invention that it can be mounted on either horizontal surfaces, such as tables, countertops and carts, or on vertical surfaces, such as walls.

It is a further feature of the present invention that it is very inexpensive to produce, facilitating its use as a disposable item.

It is yet another feature of the present invention that it can also serve as a temporary holder for a needlecap so that the needlecap can be easily found after a procedure is completed.

It is an advantage of the present invention that it is lightweight and portable, yet very stable in use.

It is another advantage of the present invention that it is particularly easy to use, its use being intuitive.

These and other objects, features and advantages of the present invention will become apparent as the description of certain representative embodiments proceeds.

SUMMARY OF THE INVENTION

The present invention provides a new needlecap holder and related method for holding a needlecap in place for safely recapping the needle on a hypodermic syringe. The breakthrough discovery of the present invention is that a simple one-piece holder can eliminate the need for a second hand to hold the needlecap without requiring modifying prior art needlecaps and hypodermic syringes. The present invention starts with a simple solid with an adhesive face that can be attached to a wall or table. Another face on the solid has an open bore sized to hold a needlecap. While the bore holds a needlecap, thus freeing the hand normally needed to hold the needlecap, the needle can be guided into the needlecap with the other hand without risk to either hand.

Accordingly, the present invention is directed to a needlecap holder comprising a solid, first and second faces on the solid, wherein the second face is at a spaced relationship from the first face, a bore in the first face extending partially through the solid toward the second face, wherein the bore is dimensioned to hold a needlecap for a hypodermic syringe, and an adhesive surface on the second face for attaching the second face to a surface. A bullseye ring may surround the opening to the bore. The first and second faces may be plane faces and the second plane face may be at an acute angle to the first plane face. The solid may have generally the shape of a rectangular solid.

The present invention is also directed to a needlecap holder comprising a solid having an axis, coaxial first and second plane faces on the solid, wherein the second plane face is at a spaced relationship from and at an acute angle to the first plane face, a bore in the first plane face extending along the axis from the first plane face partially through the solid toward the second plane face, wherein the bore is dimensioned to hold a needlecap for a hypodermic syringe, and an adhesive surface on the second plane face for attaching the face to a solid surface.

The present invention is further directed to a method for safely replacing a needlecap over a hypodermic syringe needle comprising, in order, the steps of providing a needlecap holder, the needlecap holder comprising a solid, first and second faces on the solid, wherein the second face is at a spaced relationship from the first face, a bore in the first face extending partially through the solid toward the second face, wherein the bore is dimensioned to hold a needlecap for a hypodermic syringe, and an adhesive surface on the second face for attaching the second face to a surface, attaching the second face to a surface, placing the needlecap inside the bore;, and manually guiding the needle into the needlecap until the needlecap covers the needle.

DESCRIPTION OF THE DRAWINGS

The present invention will be more clearly understood from a reading of the following detailed description in conjunction with the accompanying drawings wherein.

DETAILED DESCRIPTION

Figure 1:
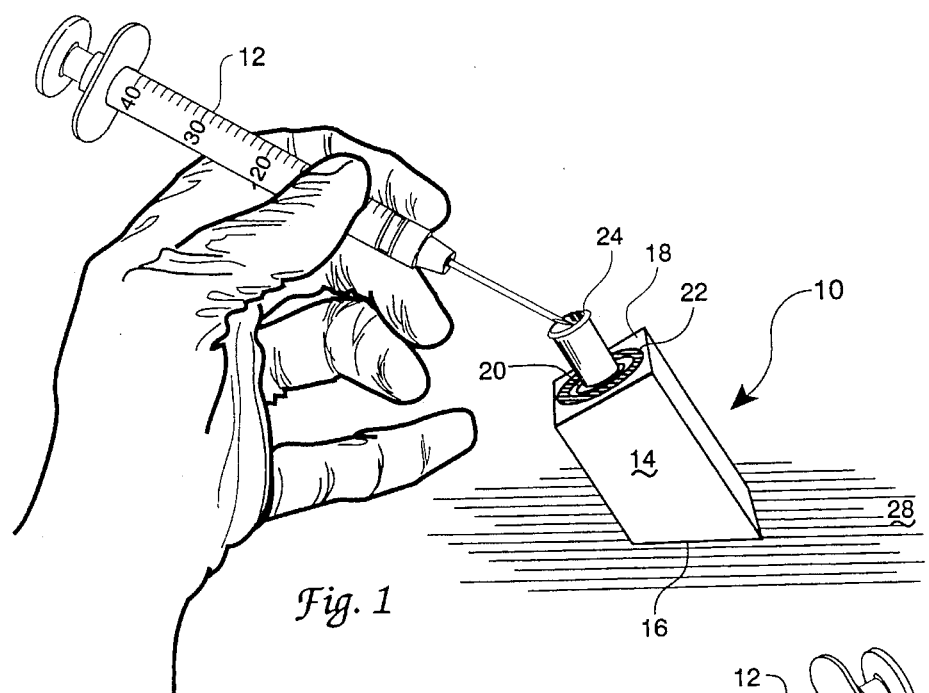
FIG. 1 is a perspective view of a needlecap holder made according to the teachings of the present invention showing its use for recapping a hypodermic syringe with the needlecap holder secured to a table.

Referring now to FIG. 1 of the drawings, there is shown a perspective view of a needlecap holder 10 made according to the teachings of the present invention showing its use for recapping a hypodermic syringe 12. In this embodiment, needlecap holder 10 is a generally rectangular solid 14 having a bottom or back face 16 at an acute angle to a top or front face 18. Front face 18 includes a bore 20 extending partially through solid 14 toward back face 16. A bullseye ring 22 surrounds bore 20. Bullseye ring 22 is a contrasting color or pattern from the rest of front face 18. Bore 20 is dimensioned to hold a conventional needlecap 24. Back face 16 includes an adhesive pad 26 (visible in FIG. 3) for attaching needlecap holder 10 to a flat surface. FIG. 1 shows needlecap holder 10 attached to a horizontal surface 28 such as a table.

Figure 2:
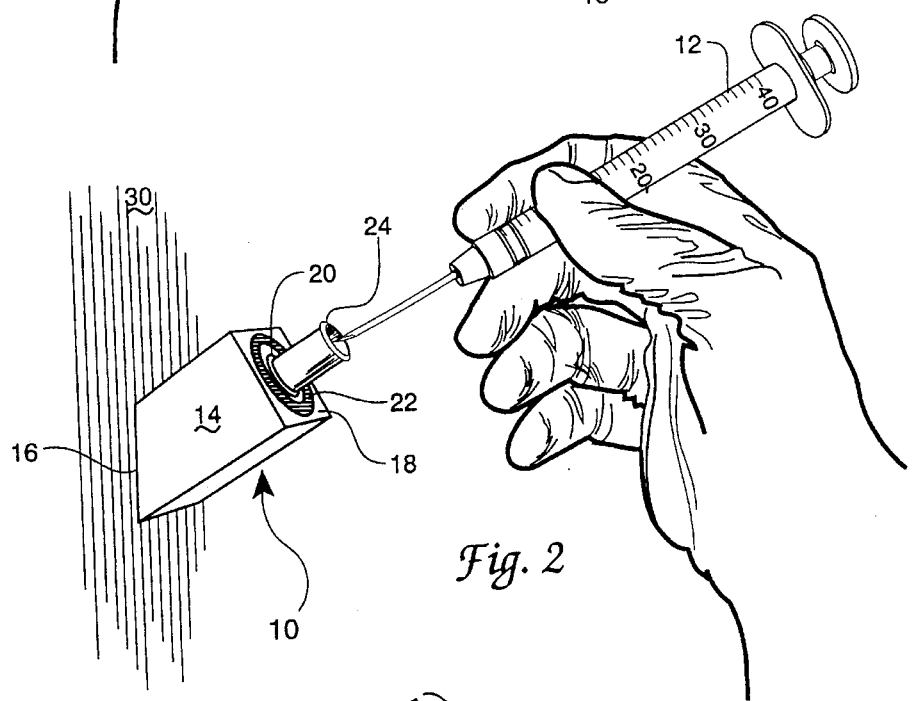
FIG. 2 is a perspective view of a needlecap holder made according to the teachings of the present invention showing its use for recapping a hypodermic syringe with the needlecap holder secured to a wall; and, FIG. 3 is a side plan view of the needlecap holder of FIGS. 1 and 2 showing its bore and an adhesive surface for attaching to a horizontal or vertical surface.

FIG. 2 shows needlecap holder 10 attached to a vertical surface 30 such as a wall.

Figure 3:
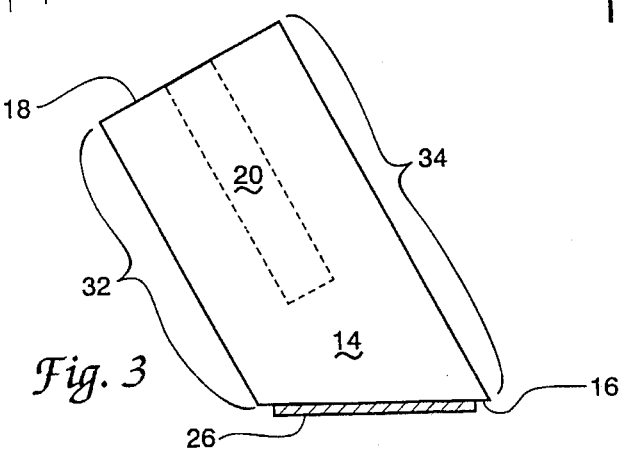

FIG. 3 is a side plan view of needlecap holder 10 of FIG. 1 showing its bore and an adhesive surface 26, such as doublesided foam tape, for attaching the holder to a wall or table. The dimensions of front face 18 of needlecap holder 10 are 25 mm×25 mm. Bore 20 has a nominal diameter of 5 mm and extends 35 mm into needlecap holder 10. The short side 32 of needlecap holder 10 is 38 mm long and the long side 34 is 50 mm long.

The use of needlecap holder 10 is intuitive. A protective covering over adhesive surface 26 is peeled off and needlecap holder 10 pressed into position on a convenient horizontal or vertical surface. After being removed from a hypodermic syringe 12, needlecap 24 is placed into bore 20 of needlecap holder 10. Besides protecting against needlestick accidents, needlecap holder 10 provides a convenient place to keep the needlecap during a procedure so that it does not become mislaid. After a procedure using syringe 12 is finished, a healthcare worker needs only one hand to guide the needle back inside needlecap 24, pressing until it snaps into place. Bullseye ring 22 helps guide the healthcare worker's aim to make the use of needlecap holder 10 even more intuitive.

Needlecap holder 10 is made of STYROFOAM and weighs about 100 grams. One advantage of styrofoam, or a similar material, is that in the event a healthcare worker misses the needlecap, the needle will have a tendency to stick into the styrofoam and not slide along a surface to accidentally stick something else. Another advantage of styrofoam is that it is light, making its attachment to vertical surfaces more sure. A further advantage is that it is inexpensive and reasonably crushable, making its disposal more convenient. Stone or metal could be used as an alternative material so that the needlecap holder could be left on a horizontal surface much like a conventional paperweight, with its weight helping to hold its position instead of an adhesive surface. Because such a holder would not be disposable, however, it may not find much use in the present healthcare environment.

The needlecap holder need not be shaped like a rectangular solid as shown, but may be cylindrical or nearly any other shape. For such other shapes, the bottom surface preferably should be flat to better attach to a flat surface and the axis of the bore preferably should be generally perpendicular to the plane of the bottom surface and along a line drawn through its center so that the force of recapping will tend to make the needlecap holder more secure and not tend to move it about. Another preference is that the back or bottom face be at an angle to the front face so that the needlestick holder can be mounted to either a horizontal or a vertical surface and still present the bore at a convenient angle to the healthcare worker. All the other surfaces, including the top or front face, may be of nearly any shape. Optionally, the front face could be shaped to deflect a needle missing the needlecap in a desired direction.

The disclosed needlecap holder successfully demonstrates the advantage of a holder for single-handed recapping of hypodermic syringes that does not require complex components to protect a second hand holding a needlecap, or complex modifications to conventional hypodermic syringes to either make them capable of one-handed recapping or to make recapping automatic. Although the disclosed holder is specialized, its teachings will find application in other areas where proposed solutions are too complex and simply will not be accepted by the workers expected to use them.

Modifications to the invention as described may be made, as might occur to one with skill in the field of the invention, within the intended scope of the claims. Therefore, all embodiments contemplated have not been shown in complete detail. Other embodiments may be developed without departing from the spirit of the invention or from the scope of the claims.

We claim:

1. A needlecap holder, comprising:
   (a) a solid having an axis;
   (b) coaxial first and second plane faces on the solid, wherein the second plane face is at a spaced relationship from and at an acute angle to the first plane face;
   (c) a bore in the first plane face extending along the axis from the first plane face partially through the solid toward the second plane face, wherein the bore is dimensioned to hold a needlecap for a hypodermic syringe;
   (d) an adhesive surface on the second plane face for attaching the face to a surface; and,
   (e) a bullseye ring on the first plane face surrounding the opening to the bore, wherein the bullseye ring is a contrasting color from the rest of the first plane face.

2. A method for safely replacing a needlecap over a hypodermic syringe needle comprising, in order, the steps of:
   (a) providing a needlecap holder, the needlecap holder comprising:
      (i) a solid;
      (ii) coaxial first and second plane faces on the solid, wherein the second plane face is at a spaced relationship from and at an acute angle to the first plane face;
      (iii) a bore in the first plane face extending along the axis from the first plane face partially through the solid toward the second plane face, wherein the bore is dimensioned to hold a needlecap for a hypodermic syringe;
      (iv) an adhesive surface on the second plane face for attaching the second plane face to a surface; and,
      (v) a bullseye ring on the first plane face surrounding the opening to the bore, wherein the bullseye ring is a contrasting color from the rest of the first plane face;
   (b) attaching the second plane face to a surface;
   (c) placing the needlecap inside the bore; and,
   (d) manually guiding the needle into the needlecap until the needlecap covers the needle.

3. A needlecap holder, comprising:
   (a) a solid having an axis;
   (b) coaxial first and second plane faces on the solid, wherein the second plane face is at a spaced relationship from and at an acute angle to the first plane face;
   (c) a bore in the first plane face extending along the axis from the first plane face partially through the solid toward the second plane face, wherein the bore is dimensioned to hold a needlecap for a hypodermic syringe;
   (d) an adhesive surface on the second plane face for attaching the face to a surface; and,
   (e) a bullseye ring on the first plane face surrounding the opening to the bore, wherein the bullseye ring is a contrasting pattern from the rest of the first plane face.

4. A method for safely replacing a needlecap over a hypodermic syringe needle comprising, in order, the steps of:
   (a) providing a needlecap holder, the needlecap holder comprising:
      (i) a solid;
      (ii) coaxial first and second plane faces on the solid, wherein the second plane face is at a spaced relationship from and at an acute angle to the first plane face;
      (iii) a bore in the first plane face extending along the axis from the first plane face partially through the solid toward the second plane face, wherein the bore is dimensioned to hold a needlecap for a hypodermic syringe;
      (iv) an adhesive surface on the second plane face for attaching the second plane face to a surface; and,
      (v) a bullseye ring on the first plane face surrounding the opening to the bore, wherein the bullseye ring is a contrasting pattern from the rest of the first plane face;
   (b) attaching the second plane face to a surface;
   (c) placing the needlecap inside the bore; and,
   (d) manually guiding the needle into the needlecap until the needlecap covers the needle.

* * * * *